United States Patent
Mitha et al.

[11] Patent Number: 5,967,153
[45] Date of Patent: Oct. 19, 1999

[54] EMULSION COATED DENTAL FLOSS CONTAINING CHEMOTHERAPEUTIC ACTIVE AGENTS

[75] Inventors: Amin S. H. Mitha, San Jose; Casper W. Chiang, Danville, both of Calif.

[73] Assignee: Gillette Canada Inc., Kirkland, Canada

[21] Appl. No.: 08/732,637

[22] Filed: Oct. 15, 1996

[51] Int. Cl.$^6$ ................................................ A61C 15/00
[52] U.S. Cl. ............................................. 132/321; 424/49
[58] Field of Search ............................ 132/321; 424/49, 424/52

[56] References Cited

U.S. PATENT DOCUMENTS

| | | | |
|---|---|---|---|
| 3,777,759 | 12/1973 | Oehmke et al. | 604/366 |
| 3,838,702 | 10/1974 | Standish et al. | 132/321 |
| 4,029,113 | 6/1977 | Guyton | 132/321 |
| 4,683,133 | 7/1987 | Southard | 424/49 |
| 5,113,880 | 5/1992 | Honda et al. | 132/321 |
| 5,209,251 | 5/1993 | Curtis et al. | 132/321 |
| 5,393,516 | 2/1995 | Rheinberger et al. | 424/52 |

FOREIGN PATENT DOCUMENTS

| | | |
|---|---|---|
| 0 000 637 | 2/1978 | European Pat. Off. |
| 0 637 446 A1 | 2/1993 | European Pat. Off. |
| WO 91/14412 | 11/1991 | WIPO . |
| WO 92/10978 | 7/1992 | WIPO . |

*Primary Examiner*—John J. Wilson
*Attorney, Agent, or Firm*—Chester Cekala

[57] ABSTRACT

Formulations of emulsified wax, surfactants, water, and chemotherapeutic agents coated onto dental floss for delivery to the oral cavity and released upon use by the consumer. Such emulsion coatings allow a single bath system and thereby improves the efficiency and effectiveness of manufacturing. In addition, the emulsified coatings reduce the level of fraying.

3 Claims, 1 Drawing Sheet

EMULSION COATED DENTAL FLOSS CONTAINING CHEMOTHERAPEUTIC ACTIVE AGENTS

BACKGROUND OF THE INVENTION

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended. Dental flosses may include distinct regions, for example, a thickened "brush" portion, a thin "floss" portion, and/or a threader. The brush portion, when drawn between tooth surfaces, provides good cleaning action which removes materials left by a standard thin floss used alone. The threader portion allows the floss to be inserted in a tight space or into an artificial dental appliance.

Dental flosses, both in brush and thin floss form, have been developed that are coated with wax in order to improve durability, feel, and frictional qualities. Waxed dental flosses containing active agents are also known in the art, and in addition to providing for the mechanical removal of food deposits from the internal spaces between teeth, also provide for the release of active agents that will act within the oral environment. Such active agents may prevent tooth decay, or have anti-tartar, antibiotic, antimicrobial, anti-inflammatory, antioxidant, or antiseptic actions.

Active agents added to wax have been found to be problematic due to inefficient release from the insoluble wax. Thus, soluble waxes such as polyethylene glycol-derivative waxes have been use. However, soluble waxes also present problems resulting from harsher sliding and decreased comfort to the user.

The use of emulsified wax has been found to improve waxed floss by allowing an improved efficiency of release of an associated chemotherapeutic product while preserving the comfortable effect obtained with insoluble wax. EP 0637 446 A1 describes a dental floss coated with emulsified wax impregnated with chemotherapeutic agents useful in oral hygiene.

A number of methods for coating wax onto dental floss are known to the art. For example, U.S. Pat. No. 3,838,702 describes a method of guiding a fiber through a liquid bath of the coating material in which the coating material is dissolved in a solvent, and then passing the coated fiber through a heated die or extruder to remove excess coating material and/or to cure the coating with evaporation of the solvent. PCT patent publication WO92/10978 describes a method of coating a dental filament with wax by using a lick roller. The lick roller is immersed in a wax solution and coats the filament with a layer of wax upon contact with the filament.

Methods of incorporating additives in dental floss are known. For example, methods for impregnating dental floss with a flavoring agent are known in the art, and include direct application with flavor oil-solvent solutions and direct contact with flavor oil in a melted wax solution. Other common additives include mouth conditioning agents such as silicones, cleaners, and abrasives, and desensitizing agents such as strontium chloride. See, for example, PCT patent application publication WO 91/14412.

Existing methods for applying both a chemotherapeutic agent and flavor require a two-step process in which a chemotherapeutic agent, either suspended in an oil phase or dissolved in an aqueous phase, is first applied to the dental floss, followed by application of a flavoring agent dissolved in oil. FIGS. 1A and 1B illustrate typical two-step methods for applying a chemotherapeutic agent and flavor-coating to a dental floss.

There is a need for a more efficient method of applying a chemotherapeutic agent and flavor to dental floss.

SUMMARY OF THE INVENTION

The present invention provides emulsion formulations for coating dental floss having one or more chemotherapeutic active and/or flavoring ingredients which are coated onto the floss and are efficiently released in the oral cavity during use. The formulation of the invention is an emulsion comprising both an oil phase and a water phase. The desired chemotherapeutic agent is solubilized in the aqueous phase, and the flavor is solubilized in the oil phase. The emulsion is formed which contains chemotherapeutic agent-containing aqueous droplets within the hydrophobic phase. The emulsion is applied to the dental floss in a single step. Upon use, the chemotherapeutic agent is released into the oral cavity of the user.

Accordingly, in one aspect, the invention features an emulsion wax formulation comprising microcrystalline wax, one or more surfactants active as emulsifying agents, a chemotherapeutic agent and a flavoring agent. The formulation of the invention may include additional additives, including other chemotherapeutic agents, flavorings, and colorings.

A variety of waxes are useful in the emulsion, so long as the wax chosen has a melting point below 100° C. and above 50° C. Useful waxes include paraffin wax, beeswax, and polyethylene glycols.

A useful chemotherapeutic agent is a compound providing a desired activity, e.g., anti-caries, anti-tartar, and/or anti-microbial activities. In a preferred embodiment, the chemotherapeutic agent is selected from the group comprising chlorohexidine, chlorohexidine derivative, stannous fluoride, sodium fluoride, triclosan, and cetyl pyridinium chloride.

In one specific embodiment, the invention provides an emulsion wax comprised of about 50% microcrystalline wax LMP; a surfactant mixture of approximately 20% sorbitan monostearate (Span 60) and 10% Tween 60; 4% sodium monofluorophosphate; and 15% deionized water.

In a second specific embodiment, an emulsion wax is provided having approximately 52% microcrystalline wax; a surfactant mixture of approximately 21% sorbitan monostearate (Span 60) and 10% Tween 60; 2% stannous fluoride; and 15% deionized water.

In a third specific embodiment, the invention provides a flavored emulsion wax formula for coating dental floss comprising approximately 53% microcrystalline wax; a surfactant mixture of approximately 7% sorbitan monostearate (Span 60) and 3% Tween 60; 2% stannous fluoride; 0.4% sodium saccharin; 19% mint flavoring; and 15% deionized water.

The invention features a dental floss coated with an emulsified wax formulation. In a specific embodiment, the waxed floss provides 0.15 mg fluoride released within the oral cavity per meter of floss.

The invention features a single bath method for coating dental floss with emulsified wax containing chemotherapeutic agents. The single bath system of the invention improves the efficiency and effectiveness of manufacturing. Generally, the single bath method of the invention comprises (a) melting a wax having a melting temperature greater than 50° C. and below 100° C., (b) adding lipid soluble agent(s), e.g., flavor, (c) adding an aqueous solution comprising desired water-soluble agents, e.g., chemotherapeutic agents to form an emulsion having aqueous droplets contained in the melted wax, (d) coating the dental floss with the emulsion, and (e) cooling the wax coating quickly. Cooling over the line distance between coating and winding may be achieved by one or a combination of air cooling and/or some sort of refrigeration. Cooling of at least the outer layer of the coating is preferably achieved in less than about one minute. The aqueous drug-containing droplets remain suspended in the dried wax coating. Upon use of the dental floss, the droplets are crushed, dissolved, and penetrated and the chemotherapeutic agent released into the oral cavity.

Although the invention is directed towards being capable of combining water-based chemotherapeutic agents and oil-based flavors for application to dental floss in one bath-coating step, the coating step may be repeated by using two dip tanks or lick rollers in series to achieve a higher level of coating.

In addition to providing an improved emulsified wax coating for dental floss and an improved method of manufacture, the invention provides a method of reducing the fraying of dental floss.

These and other features and advantages of the invention will become apparent to those persons skilled in the art upon reading the details of the compositions and methods of the invention as more fully described below.

DETAILED DESCRIPTION

Before the present compositions and methods of use are described, it is to be understood that this invention is not limited to particular compositions or methods described, as such compositions and methods may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

Emulsifying Wax Formulations

The present invention provides a dental floss having an emulsified wax coating which releases chemotherapeutic agents into the oral cavity upon contact with saliva.

Figure 1A:
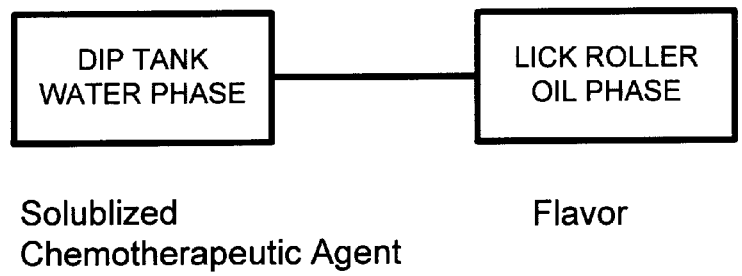
FIG. 1A is a diagram illustrating an existing chemotherapeutic and flavoring agent application process in which the chemotherapeutic agent is solubilized in an aqueous phase contained in a dip tank and the flavoring agent is solubilized in an oil phase on a lick roller.
Figure 1B:
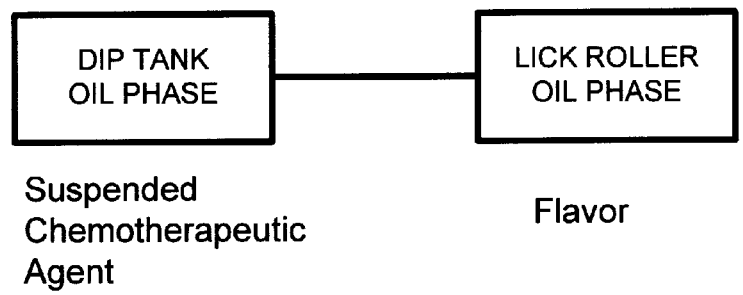
FIG. 1B is a diagram illustrating an existing chemotherapeutic and flavoring agent application process in which the chemotherapeutic agent is suspended in the oil phase contained in a dip tank and the flavoring agent is solubilized in an oil phase on a lick roller.

The invention further includes a single bath method for applying a chemotherapeutic agent and flavor to a dental floss in a single coating step. As shown in FIGS. 1A–1B, existing methods for applying a chemotherapeutic agent to a dental floss generally use a two-step method. In one typical method, a water-soluble chemotherapeutic agent is applied to floss in a dip tank containing an aqueous solution of the chemotherapeutic agent, followed by processing of the floss through a lick roller for application of a flavoring agent dissolved in an oil phase (FIG. 1A). Alternatively, a chemotherapeutic agent is suspended in a oil phase which is contacted with the dental floss in a dip tank, followed by processing of the floss through a lick roller which applies the flavoring agent (FIG. 1B).

Figure 2:
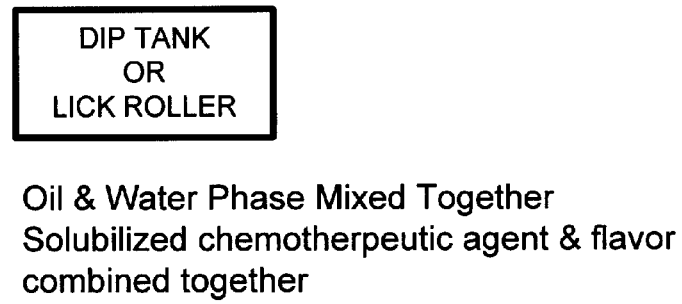
FIG. 2 is a schematic illustrating the solubilized chemotherapeutic agent and flavoring agent in the emulsified formulation of the invention which is applied to the dental floss in a single application through a dip tank or a lick roller.

By contrast, the preferred formulation of the invention contains both an oil phase and a water phase mixed together, e.g., emulsified, and in which the chemotherapeutic agent and flavoring agent are combined (FIG. 2). This formulation allows both components to be applied to the dental floss in a single step, thus improving the efficiency of production by eliminating a step in manufacture.

The preferred emulsified wax formulation of the invention comprises microcrystalline wax with one or more emulsifying (or lubricating) agents, flavor(s), and chemotherapeutic agents.

Emulsifying waxes. The components of the emulsified wax formulation of the invention are necessarily non-toxic and safe for oral use. A variety of waxes known to the art may be selected. However, the wax chosen must have a melting point below 100° C., as higher melting point waxes would result in excessive loss of the water content of the formulation upon melting of the wax to form the emulsion of the invention. The melting point of the wax must also be higher than 50° C. for adequate shelf stability and maintenance of solidification. The melting point of the wax chosen will vary depending on the choice of ingredients and the wax chosen. Examples of suitable waxes include natural and synthetic waxes; preferably microcrystalline wax such as paraffin, beeswax, or polyethylene glycols. Suitable waxes may be identified with use of the industry standard ingredient dictionary published by the Cosmetic, Toiletry & Fragrance Association (CTFA).

Emulsifying agents. The emulsifying agent (surfactant) component of the formulation of the invention provides that the wax formulation will remain stable as a homogeneous composition for the period of time required to form the emulsion and coat the emulsion onto the dental floss. The stability of the formulation is dependent both on the choice of ingredients and surfactant systems familiar to those skilled in the art.

In the method of the invention, the emulsion of the invention is formed by use of the hydrophile-lipophile balance (HLB) system, a system known to one of ordinary skill. For emulsification of the oil phase, the surfactant chosen depends on the specific flavor, wax and required HLB. The surfactant chosen will also affect the release of the chemotherapeutic agent and the type of chemotherapeutic agent chosen, as will be recognized by those skilled in the art. A listing of candidate surfactants may be found in the CTFA ingredient dictionary. Surfactants useful in the invention may be cationic, anionic, or non-ionic (zwitterionic), and may be solid or liquid at room temperature. Preferably the surfactant chosen would be approved for human consumption. Suitable surfactants for use in the formulation of the invention include, for example, SPAN®, ARALCEL®, TWEEN®, BRIJ®, and MYRJ® (ICI Chemicals).

Chemotherapeutic and active agents. The formulation of the invention contains one or more chemotherapeutic agents having anti-caries, anti-tartar, and/or anti-microbial activities to promote oral health. Preferred chemotherapeutic agents include, for example, chlorohexidine and chlorohexidine derivatives, stannous fluoride, sodium fluoride, sodium monofluorophosphate, triclosan, cetyl pyridinium chloride (CPC), and other agents familiar to those skilled in the art.

Flavorings and sweeteners. Flavors, sweeteners, and colorants are used to impart optimum cosmetic characteristics to the compositions of the invention. Generally, the flavoring component is present as an oil, emulsified into the composition by the emulsifying agent components.

Conventional flavoring components include menthol, anise oil, benzaldehyde, bitter almond oil, camphor, cedar leaf oil, cinnamic aldehyde, cinnamon oil, citronella oil, clove oil, eucalyptol, heliotropin, lavender oil, mustard oil, peppermint oil, phenyl salicylate, pine oil, pine needle oil, rosemary oil, sassafras oil, spearmint oil, thyme oil, thymol, wintergreen oil, lemon and orange oils, vanillin, spice extracts, and other flavoring oils generally regarded as safe by health officials.

Suitable sweetening agents include sorbitol, sodium cyclamate, saccharine, aspartame, acesulfame K, glyceryhyzzinic acid, and xylitol.

Dental floss. The dental floss to be coated may be composed of any suitable natural or synthetic filamentous material, for example, cotton, silk, linen, nylon, polyester, or acrylic, or mixtures thereof. The floss may be round or flat, and may be composed of braided, spun, or twisted fibers capable of being inserted between teeth. The fiber to be coated is preferably a multi-filament fiber having sufficient strength to be easily used by the consumer without breaking. The dental flosses usable in the invention include bulked and non-bulked fibers. The term "dental floss" includes dental flosses, dental tapes, and similar articles.

Dental filaments for use in the flosses of the invention are manufactured preferably as multicomponent coextruded filaments. By "multicomponent" is meant a filament having two or more components; by "coextruded" is meant that at least two of the components are present in the form of substantially separate phases having a distinct interface between them, rather than being intermixed. The filaments may be formed by processes referred to in the art as "coextruded", but may also encompass filaments having the structure described above which are manufactured by other processes known to the art.

Single Bath Coating System

The coating of solid material onto a dental material, such as dental floss, is generally achieved by dissolving the coating material in a solvent such as ethanol, acetone, ethyl acetate, or triethylene glycol. Commonly used natural and synthetic resins are generally dissolved in a solvent, and the resin becomes hard after evaporation of the solvent. Examples of commonly used resins are shellac, benzoin resin, polyvinyl pyrrolidone, and colophony. U.S. Pat. No. 5,393,516 describes the coating of dental material with an antibacterial chlorhexidine adduct. The chlorhexidine adduct is formulated into a light-curing sealant applied with a paint-brush onto a molar fissure.

The single bath method of the invention provides several advantages over conventional two-step methods. The method presented here does not use solvent, and thus avoids the health and environmental problems associated with solvent use. Additionally, the single step method of coating dental floss provides an improved efficiency of manufacturing. The chemotherapeutic agent is dispersed in the water droplets and bound in the wax matrix until released therefrom through solubilization or abrasion.

The invention features a single bath method for coating dental floss with emulsified wax containing chemotherapeutic agents. The single bath system of the invention improves the efficiency and effectiveness of manufacturing. Generally, the single bath method of the invention comprises (a) melting a wax having a melting temperature greater than 50° C. and below 100° C., with a preferred range of 55 to 65° C.; (b) adding lipid-soluble agent such as a flavor which is emulsified along with the rest of the lipid ingredients; (c) adding an aqueous solution comprising one or more desired water-soluble chemotherapeutic agents to form an emulsion having aqueous chemotherapeutic agent-containing droplets contained in the melted wax; (d) coating the dental floss with the emulsion; and (e) cooling the wax coating quickly. Flavorings may also be added to the emulsion.

The emulsion compositions described in Example 1 were coated onto dental floss as described, and tested for fluoride release and fraying. Dental floss coated with emulsified wax formulation composition A containing fluoride in the form of monofluorophosphate (MFP) showed low fray values; however the fluoride release measurement was poor because the fluoride was primarily released indirectly as monofluorophosphate and not directly as fluoride as with stannous fluoride or sodium fluoride: The test method used to detect fluoride release (described below) was better at measuring fluoride released directly rather than indirectly as monofluorophosphate.

Dental floss coated with emulsified wax formulation composition B containing fluoride in the form of stannous fluoride had slightly higher fray values, due largely to the high coating level. The fluoride release of this formulation was better than the release achieved with composition A (see Table 1 below). Dental floss coated with emulsified mint wax formulation composition C containing fluoride in the form of stannous fluoride had low fray values and better fluoride release than that of composition A. From these results, an emulsified wax composition containing fluoride which releases as fluoride rather than as monofluorophosphate and has low fray values is preferred.

EXAMPLES

The following examples are put forth so as to provide those of ordinary skill in the art with a complete disclosure and description of how to make and use the compositions and methods of the invention, and are not intended to limit the scope of what the inventors regard as their invention. Efforts have been made to ensure accuracy with respect to numbers used (e.g., amounts, temperatures, etc.) but some experimental error and deviations should be accounted for. Unless otherwise indicated, temperature is in degrees Centigrade, molecular weight is average molecular weight, and pressure is at or near atmospheric.

Example 1

Emulsified Wax Formulations

A beaker containing the microcrystalline wax and selected surfactants described below for each formulation was warmed with stirring in a water bath until melted. An aqueous solution containing either sodium monofluorophosphate or stannous fluoride was added dropwise to the melted wax/surfactant mixture dropwise, optionally followed by an aqueous solution of sodium saccharide, and flavor in oil. Stirring continuously, the resulting emulsion was removed from heat and was applied onto dental floss by dipping the floss into the melted emulsion.

Composition A (emulsified wax, no flavor) (weight %) 50.08% microcrystalline wax LMP (Shell-Holland), 21.09% sorbitan monostearate (Span 60) (ICI Chemicals), 9.92% Tween 60 (ICI Chemicals), 4.00% sodium monofluorophosphate (Ozark-Mahoning) (active ingredient), 14.91% deionized water.

Composition B (emulsified wax, no flavor) (weight %) 52.01% microcrystalline wax, 21.09% sorbitan monostearate (Span 60), 9.92% Tween 60, 2.07% stannous fluoride (Ozark-Mahoning) (active ingredient), 14.91% deionized water.

Composition C (emulsified wax, flavor) (weight %) 53.11% microcrystalline wax, 6.876 sorbitan monostearate (Span 60), 3.22% Tween 60 2.07% stannous fluoride (active ingredient), 0.40% sodium saccharin (PMC), 19.18% mint flavoring, 15.15% deionized water.

Fluoride release. Fluoride release was measured as sodium monofluorophosphate or stannous fluoride using the method next described. Fluoride in emulsified wax composition A was released primarily as monofluorophosphate.

To measure fluoride release for a dental floss according to Oral-B internal testing procedure DF-09 (Rev. D), working 100 ml standard solutions in 50:50 TISAB/Water were prepared in concentrations of 2.8, 3.2, 3.4, and 3.8 mg NaF/100 ml. TISAB is 1,2-cyclohexanediamine-tetraacetic acid (CDTA), available from ATI Orion. A potentiometer coupled to a fluoride ion-specific electrode was then used to measure the mV value of each working standard after a 90-second stabilization period, and all mV readings were plotted on the x-axis against the log concentration of mg NaF/100 ml standard. A correlation coefficient, R (>0.999), using the linear regression function was then calculated. It was important to allow the fluoride ion-specific electrode to stabilize in a 100 ppm fluoride solution for at least one hour before use; otherwise, the R value of the standard curve was low and had to be repeated.

Then, for each of twenty dental floss bobbins from the same lot, approximately the first two meters of floss on each bobbin were discarded; the next half (0.5) meter of fluoridated floss on each bobbin was removed; all twenty half-meter samples were immersed in 100 ml of 50:50 TISAB/Water; the solution was vigorously stirred for one minute; the fluoride ion-specific electrode was then placed in the solution and its stabilized mV value was read after 90 seconds of gentle stirring; the mV reading was plotted against the calibrated curve, and the corresponding [mg NaF] reading was determined, interpolating as necessary. This value was then divided by the number of source bobbins to yield [mg NaF/0.5 meters of floss]. The results are shown in Table 1:

TABLE 1

| ANALYSIS | A | B | C |
|---|---|---|---|
| Coating (weight %, coating:raw yarn) | 27.83 | 58.55 | 36.53 |
| Fluoride (mg/0.5 m$^1$) | 0.0019$^a$ | 0.426$^b$ | 0.337$^b$ |
| Fray | 0.9 | 2.35 | 0.9 |

$^a$measured as monofluorophosphate (MFP)
$^b$measured as stannous fluoride (SnF$_2$)

Fray values for a dental floss were measured in vitro according to Oral-B internal testing procedure DF-26 (Rev. C) using the Oral-B Manual Fray Tester which simulates actual floss use. Floss is moved through a tight opening between two porcelain molar teeth manufactured by Kilgore Int'l (catalog No. B3305, Nos. 1 and 2), held together with a 1-pound compression force, with a repeated up-and-down motion. More specifically, the dental floss was inserted, and withdrawn from, between the mounted teeth for 25 cycles over 6–7 seconds using an Instron while under tension from a 500-gram weight; the number of broken ends of filaments on one side only was then determined. 20 samples of each type of floss were tested, yielding an average.

The fray values of the emulsified wax coated floss of the invention compared favorably with, and showed some improvement over, the fray values of other comparable flosses commercially available to date. For example, Oral-B Mint Wax Fluoride Dental Floss had a fray value of 4.1 without the benefit of the invention as compared to a fray value of 0.9 of a floss encompassed by the invention. See Table 1.

What is claimed is:

1. A dental floss coated with an emulsion wax formulation comprising about 50% microcrystalline wax LMP (w/w), about 20% sorbitan monostearate (w/w), 10% polysorbate 60 (w/w), about 4% sodium monfluorophosphate (w/w) and about 15% deionized water (w/w).

2. A dental floss coated with an emulsion wax formulation comprising about 52% microcrystalline wax (w/w), about 21% sorbitan monostearate (w/w), about 10% polysorbate 60 (w/w), about 2% stannous fluoride (w/w) and about 15% deionized water (w/w).

3. A dental floss coated with an emulsion wax formulation comprising about 53% microcrystalline wax (w/w), about 7% sorbitan monostearate (w/w), about 3% polysorbate 60 (w/w), about 2% stannous fluoride (w/w) and about 0.4% sodium saccharin (w/w), about 19% mint flavoring (w/w) and about 15% deionized water (w/w).

* * * * *